United States Patent
Simon et al.

(10) Patent No.: US 7,091,396 B1
(45) Date of Patent: Aug. 15, 2006

(54) ANIMALS, CELLS AND METHODS FOR PRODUCTION OF DETECTABLY-LABELED ANTIBODIES

(75) Inventors: Sanford M. Simon, New York, NY (US); Yu Chen, New York, NY (US)

(73) Assignee: The Rockefeller University, New York, NY (US)

( * ) Notice: Subject to any disclaimer, the term of this patent is extended or adjusted under 35 U.S.C. 154(b) by 78 days.

(21) Appl. No.: 09/982,120

(22) Filed: Oct. 17, 2001

Related U.S. Application Data

(60) Provisional application No. 60/241,053, filed on Oct. 17, 2000.

(51) Int. Cl.
*A01K 67/027* (2006.01)
*A01K 67/033* (2006.01)
*C12N 15/63* (2006.01)
*C12N 5/06* (2006.01)
*C12N 5/10* (2006.01)

(52) U.S. Cl. .......................... 800/18; 800/13; 435/326; 435/325; 435/455; 435/320.1

(58) Field of Classification Search .................. 800/13, 800/18; 435/325, 326, 320.1, 455
See application file for complete search history.

(56) References Cited

U.S. PATENT DOCUMENTS 5,202,238 A * 4/1993 Fell et al. .................. 435/69.6
6,570,061 B1 * 5/2003 Rajewsky et al. ............ 800/18

OTHER PUBLICATIONS

Casey et al. (2000) Prot. Engineer., vol. 13 (6), 445-452.*
Casey, Joanne L. et al. Protein Engineering vol. 13 (No. 6); pp. 445-452 (2000) "Green Fluorescent Antibodies: novel *in vitro* tools".

* cited by examiner

*Primary Examiner*—Anne Marie S. Wehbe'
(74) *Attorney, Agent, or Firm*—Klauber & Jackson

(57) ABSTRACT

Genetically-modified mammals and immune cells are provided which are capable of producing or secreting detectably-labeled immunoglobulin molecules as a result of genetic modifications of at least one immunoglobulin gene in the genome thereof, such that a fusion polynucleotide encoding a detectable protein or peptide and an immunoglobulin component molecule is present.

31 Claims, 3 Drawing Sheets

US 7,091,396 B1

ANIMALS, CELLS AND METHODS FOR PRODUCTION OF DETECTABLY-LABELED ANTIBODIES

CROSS-REFERENCE TO RELATED APPLICATION

This application claims priority under 35 U.S.C. § 119(e) to provisional application Ser. No. 60/241,053, filed Oct. 17, 2000, which is incorporated herein by reference in its entirety.

FIELD OF THE INVENTION

The invention is directed to methods for obtaining detectably-labeled antibodies to any antigen by using genetically-modified mammals which express at least one detectably-labeled antibody molecule component.

BACKGROUND OF THE INVENTION

Antibodies are widely used for diagnostic and research purposes for localizing an antigen within a cell, tissue, or other biological sample. For histopathology or cytology, cells are usually first exposed to a primary antibody which is specific for the desired target antigen but not directly detectable. In a subsequent step, the primary antibody is detected with a labeled secondary antibody which recognizes the primary antibody. This procedure is somewhat cumbersome and may result in undesirable background staining due to non-specific reactivity of the secondary antibody. In addition, in order to visualize two or more antigens, the primary antibodies must be from two different species such that each secondary antibody is not cross-reactive; expensive species-specific secondary antibodies must therefore be used for each primary antibody. With advances in optical and digital imaging and detection, multiply-labeled samples and simultaneous detection of several analytes is possible, yet the aforementioned biological limitations do not permit full advantage to be taken of these advances. Moreover, since 99 monoclonal antibodies are generated typically only in mice and rats, in conventional dual or triple labeling, only one antibody can be monoclonal. This can be an important restriction.

Several techniques are available to circumvent these limitations, including direct chemical conjugation of the primary antibody with a detectable molecule, or direct conjugation with biotin and subsequence detection with a fluorescent avidin. These procedures are cumbersome and requires purification of the primary antibodies.

It is towards the facile preparation of a detectable primary antibody to any desired antigen that the present invention is directed.

The citation of any reference herein should not be construed as an admission that such reference is available as "Prior Art" to the instant application.

SUMMARY OF THE INVENTION

In one broad aspect, the invention is directed to a genetically-modified mammal capable of expressing at least one chimeric immunoglobulin gene comprising at least one detectable protein or peptide fused with a gene expressing an immunoglobulin component selected from the group consisting of the kappa immunoglobulin light chain, the lambda immunoglobulin light chain, an immunoglobulin heavy chain, and any combination thereof, wherein antibodies secreted by immune cells of the genetically-modified mammal comprise said at least one detectable protein or peptide. The immunoglobulin heavy chain gene may be IgG, IgM, IgD or IgA. In one embodiment, the at least one detectable peptide or protein is present at the C-terminus of the gene product of the fusion polynucleotide; preferably, the at least one detectable peptide or protein present at the C-terminus of the gene product of the fusion polynucleotide is located in exon G1. In another embodiment, the at least one detectable peptide or protein is present at the C-terminus of the gene product of the fusion polynucleotide with a flexible linker peptide therebetween. Preferably, the least one detectable peptide or protein present at the C-terminus of the gene product of said fusion polynucleotide with a flexible linker therebetween is located in exon G1.

In one embodiment, the immunoglobulin molecule secreted by immune cells of the above-mentioned genetically-modified mammal comprises at least one detectable protein or peptide in the heavy chain of the immunoglobulin molecule. In another embodiment, the immunoglobulin molecule secreted by immune cells of the genetically-modified mammal comprises at least one detectable protein or peptide in the light chain of said immunoglobulin molecule. In a further embodiment, the immunoglobulin molecule secreted by immune cells of the genetically-modified mammal comprises at least one detectable protein or peptide in the heavy chain and at least one detectable protein or peptide in the light chain of said immunoglobulin molecule.

In one embodiment of the invention, at least one of the aforementioned detectable proteins or polypeptides is an autofluorescent protein or peptide, a visibly-detectable protein or peptide, an enzymatically active protein or peptide, a protein or peptide capable of interacting with another molecule to produce a detectable product, or any combination thereof. In another embodiment, the detectable protein or polypeptide is capable of quenching or modulating fluorescence. Non-limiting examples of autofluorescent proteins or peptides include green fluorescent protein, red fluorescent protein, and a fluorescent analog or fragment of any of the foregoing. Green fluorescent protein is preferred. In another embodiment, the at least one detectable protein is a combination of an autofluorescent protein or peptide and an enzymatically-active protein or peptide, such as but not limited to a combination of green fluorescent protein and alkaline phosphatase.

In another broad aspect of the invention, a genetically-modified immune cell is provided which is capable of expressing at least one chimeric immunoglobulin gene comprising at least one detectable protein or peptide fused with a gene expressing an immunoglobulin component selected from the group consisting of the kappa immunoglobulin light chain, the lambda immunoglobulin light chain, an immunoglobulin heavy chain, and any combination thereof, wherein antibodies secreted by the genetically-modified immune cell comprise the at least one detectable protein or peptide. The immunoglobulin heavy chain gene may be IgG, IgM, IgD or IgA. In one non-limiting example, the at least one detectable peptide or protein is present at the C-terminus of the gene product of the fusion polynucleotide; preferably, the polynucleotide encoding the at least one detectable peptide or protein present at the C-terminus of the gene product of said fusion polynucleotide is located in exon G1. In another embodiment, the at least one detectable peptide or protein present at the C-terminus of the gene product of said fusion polynucleotide has a flexible linker peptide therebetween; preferably, the polynucleotide encoding the at least one detectable peptide or protein present at the C-terminus of the gene product of said fusion polynucleotide with a flexible linker therebetween is located in exon G1.

The immunoglobulin molecule secreted by the aforementioned immune cell may comprise at least one detectable protein or peptide in the heavy chain of the immunoglobulin molecule, or it may comprise at least one detectable protein or peptide in the light chain of said immunoglobulin molecule. In another embodiment, the immunoglobulin molecule secreted by the genetically-modified immune cells described above comprises at least one detectable protein or peptide in the heavy chain and at least one detectable protein or peptide in the light chain of the immunoglobulin molecule.

The aforementioned genetically-modified immune cell may have at least one detectable protein or polypeptide that is capable of quenching or modulating fluorescence; or the protein or peptide is an autofluorescent protein or peptide, a visibly-detectable protein or peptide, an enzymatically active protein or peptide, a protein or peptide capable of interacting with another molecule to produce a detectable product, or any combination thereof. In the example wherein the at least one detectable protein is an autofluorescent protein or peptide, it may be, by way of non-limiting example, green fluorescent protein, red fluorescent protein, or a fluorescent analog or fragment of any of the foregoing. Green fluorescent protein is preferred. In another embodiment, the at least one detectable protein is a combination of an autofluorescent protein or peptide and an enzymatically-active protein or peptide, such as but not limited to a combination of green fluorescent protein and alkaline phosphatase.

The invention is also directed to a hybridoma comprising the genetically-modified immune cell as mentioned above.

In yet another aspect, the invention is directed to a chimeric, detectably-labeled immunoglobulin molecule comprising at least one detectable protein or peptide fused with the kappa immunoglobulin light chain, the lambda immunoglobulin light chain, an immunoglobulin heavy chain, or any combination thereof. The at least one detectable peptide or protein may be present at the C-terminus of the gene product of said fusion polynucleotide, preferably located in exon G1. A flexible linker peptide may be provided therebetween. In another embodiment, a polynucleotide encoding said at least one detectable peptide or protein present at the C-terminus of the gene product of said fusion polynucleotide with a flexible linker therebetween is located in exon G1. The chimeric, detectably-labeled immunoglobulin molecule may have an immunoglobulin heavy chain gene is selected from IgG, IgM, IgD and IgA. At least one detectable protein or peptide may be present in the heavy chain of said immunoglobulin molecule, the at least one detectable protein or peptide may be present in the light chain of said immunoglobulin molecule, or, in a further embodiment, the at least one detectable protein or peptide may be present in the heavy chain and at least one detectable protein or peptide in the light chain of said immunoglobulin molecule.

The aforementioned chimeric, detectably-labeled immunoglobulin molecule may have at least one detectable protein or polypeptide that is capable of quenching or modulating fluorescence; or, the at least one detectable protein or peptide is an autofluorescent protein or peptide, a visibly-detectable protein or peptide, an enzymatically active protein or peptide, a protein or peptide capable of interacting with another molecule to produce a detectable product, or any combination thereof. In one embodiment, the at least one detectable protein is an autofluorescent protein or peptide, such as but not limited to green fluorescent protein, red fluorescent protein, or a fluorescent analog or fragment of any of the foregoing. Preferably, it is green fluorescent protein. In another embodiment, the at least one detectable protein may be a combination of an autofluorescent protein or peptide and an enzymatically-active protein or peptide, such as but not limited to a combination of green fluorescent protein and alkaline phosphatase.

In a further broad aspect, the present invention provides a method for producing a quantity of detectably-labelled polyclonal antibodies by carrying out at least the steps of
  a) providing a genetically-modified mammal as described hereinabove;
  b) immunizing the genetically-modified mammal with a preselected immunogen, wherein the genetically-modified mammal generates antibodies to the immunogen, wherein antibodies secreted by immune cells of the genetically-modified mammal comprise the at least one detectable protein or peptide; and
  c) isolating the detectably-labelled antibodies from the genetically-modified mammal.

The invention is also directed to a method for producing a quantity of detectably-labelled monoclonal antibodies comprising the steps of
  a) preparing a genetically-modified mammal in accordance with the above description;
  b) immunizing the genetically-modified mammal with a preselected immunogen, wherein immune cells of the genetically-modified mammal generate antibodies to the immunogen, wherein antibodies secreted by the immune cells comprise the at least one detectable protein or peptide;
  c) immortalizing antibody-producing immune cells isolated from the genetically-modified mammal;
  d) selecting immortalized immune cells isolated from the genetically-modified mammal that secrete antibodies specific to the immunogen; and
  e) preparing a quantity of detectably-labeled monoclonal antibodies from the selected immune cells.

In a further aspect, the invention is also directed to a genetically-modified mammal capable of producing a detectably-labeled immunoglobulin in response to immunization by an antigen, the genome of the mammal comprising at least one fusion polynucleotide consisting of a polynucleotide sequence encoding at least one detectable protein or peptide fused with a the kappa immunoglobulin light chain gene, the lambda immunoglobulin light chain gene, an immunoglobulin heavy chain gene, or any combination thereof, wherein antibodies secreted by immune cells of the genetically-modified mammal comprise the at least one detectable protein or peptide.

In a further aspect, the invention is directed to a chimeric, detectably-labeled immunoglobulin molecule comprising at least one fluorescent protein or peptide and at least one fluorescence-quenching or -modulating protein or peptide fused with a component of the immunoglobulin molecule independently selected from either the kappa immunoglobulin light chain, the lambda immunoglobulin light chain, an immunoglobulin heavy chain, or any combination thereof.

These and other aspects of the present invention will be better appreciated by reference to the following drawings and Detailed Description.

DETAILED DESCRIPTION OF THE INVENTION

Figure 1:
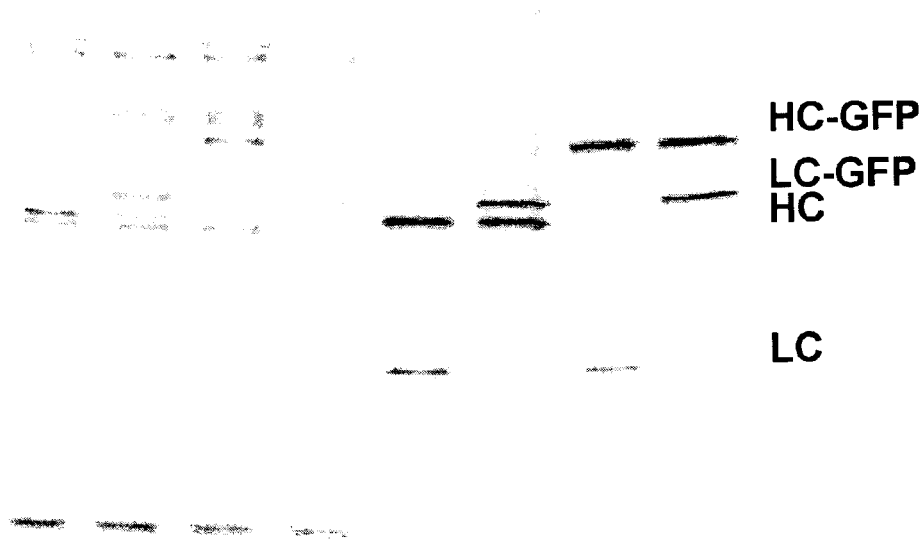
FIG. 1 shows the beta-galactosidase-binding activity of a chimeric fusion immunoglobulin secreted from 293T cells transfected with nucleic acid encoding a green-fluorescent-protein-labeled heavy immunoglobulin (IgG2) chain and a green-fluorescent-protein-labeled light (kappa) chain hybrid anti-beta-galactosidase immunoglobulin.

The inventors herein have discovered a novel and facile method for preparing useful quantities of detectably-labeled polyclonal or monoclonal antibodies to any preselected immunogen. The method spares the need to perform any modification of the immunogen-specific (primary) antibody to provide a detectable label thereon, such as conjugation to a fluorophore or enzyme, as the detectably-labeled antibodies of the invention are inherently labeled as they are expressed and secreted from genetically-modified immune system cells. In its broadest aspect, the invention provides genetically-modified animals and immune cells from such animals in which the constant region of the heavy and/or the light chain components of the antibodies produced by the animals or cells is fused with a detectable polypeptide, such as a fluorescent polypeptide, these fusion protein(s) resulting from the expression of a genetic modification of the heavy and/or light chain genes wherein the polynucleotide encoding the detectable label is incorporated into the respective genes. Such genetically-modified animals or cells are provided such that any antibody expressed and secreted by the animal or cell comprises at least one labeled constant region. Thus, the mere induction of a humoral immune response generates the desired detectably-labeled antibody.

The detectable labels of the invention are polypeptides, such as proteins or peptides, and they may be introduced into the genome of a mammalian organism by such methods as homologous recombination and transfection, but such methods are not intended to be limiting whatsoever, and one of skill in the art may prepare the construct(s) and modified cells in any appropriate manner. Embryonic stem cells may be so modified such that the genome of the animal resulting therefrom comprises the genetic modification. Several examples provided below are for illustrative purposes only.

The detectable polypeptide may be, by way of non-limiting example, a fluorescent polypeptide, a visibly-colored polypeptide, a polypeptide with enzymatic activity, or a polypeptide capable of interacting with or binding to another molecule to produce a detectable product. Preferred are labels which require no direct interaction or further sample processing for detectability, and thus are detectable by the application of exogenous methods such as absorbance of light, fluorescence, etc. More preferred are fluorescent polypeptides; most preferred is green fluorescent protein and its polypeptide relatives.

Moreover, a plurality of detectable labels may be present in the antibodies produced by the animals or cells of the invention. For example, both a fluorescent label and an enzyme label may be appended in tandem to the C-terminus of an immunoglobulin heavy chain gene, such that the resulting expressed and assembled immunoglobulin molecule is detectable both by fluorescence and by histochemistry, by use of a fluorigenic and chromogenic/precipitating substrate of the enzyme, respectively. In another example, the antibody is detectable fluorometrically and by Western blot. As noted above, either or both the heavy and light chain constant regions may be independently modified as described herein, both with the same single or plurality of labels, or, for example, the heavy chain with a fluorescent label and the light chain with an enzyme label. These particular examples of multiple labels on multiple sites of the antibodies are merely illustrative of the range of directly-labeled antibodies that the skilled artisan may be directed to prepare following the teachings herein, and any particular example or embodiment is not intended to be limiting whatsoever.

Examples of fluorescent polypeptides include but are not limited to green fluorescent protein and other related polypeptide fluorophores which may produce other colors; the availably of individually-detectable primary antibodies in a mixture allows for the simultaneous localization or quantitation of multiple target antigens or analytes in a biological sample. The green fluorescent protein of *Aequorea victoria* is particularly preferred as the fluorescent protein. A cDNA for the protein has been cloned (D. C. Prasher et al., "Primary structure of the *Aequorea victoria* green-fluorescent protein," Gene (1992)111:229–33.). *Aequorea* green fluorescent protein ("GFP") is a stable, proteolysis-resistant single chain of 238 residues and has two absorption maxima at around 395 and 475 nm; Excitation at the primary absorption peak of 395 nm yields an emission maximum at 508 nm with a quantum yield of 0.72–0.85 (O. Shimomura and F. H. Johnson J. Cell. Comp. Physiol. 59:223 (1962); J. G. Morin and J. W. Hastings, J. Cell. Physiol. 77:313 (1971); H. Morise et al. Biochemistry 13:2656 (1974); W. W. Ward Photochem. Photobiol. Reviews (Smith, K. C. ed.) 4:1 (1979); A. B. Cubitt et al. Trends Biochem. Sci. 20:448–455 (1995); D. C. Prasher Trends Genet. 11:320–323 (1995); M. Chalfie Photochem. Photobiol. 62:651–656 (1995); W. W. Ward. Bioluminescence and Chemiluminescence (M. A. DeLuca and W. D. McElroy, eds) Academic Press pp. 235–242 (1981); W. W. Ward & S. H. Bokman Biochemistry 21:4535–4540 (1982); W. W. Ward et al. Photochem. Photobiol. 35:803–808 (1982)). Mutants of GFP are embraced herein as they provide certain other characteristics, such as mutation of Serine 65 to Thr (S65T) simplifies the excitation spectrum to a single peak at 488 nm of enhanced amplitude (R. Heim et al. Nature 373:664–665 (1995)), which no longer gives signs of conformational isomers (A. B. Cubitt et al. Trends Biochem. Sci. 20:448–455 (1995)). In another example, U.S. Pat. No. 6,077,707 describes a nucleic acid molecule comprising a nucleotide sequence encoding a functional engineered fluorescent protein whose amino acid sequence is substantially identical to the amino acid sequence of *Aequorea* green fluorescent protein but differs by at least a substitution at T203 and, in particular, T203X, wherein X is an aromatic amino acid selected from H, Y, W or F. In one embodiment therein, the amino acid sequence further comprises a substitution at S65, wherein the substitution is selected from S65G, S65T, S65A, S65L, S65C, S65V and S65I. In another embodiment, the amino acid sequence differs by no more than the substitutions S65T/T203H; S65T/T203Y; S72A/F64L/S65G/T203Y; S65G/V68L/Q69K/S72A/T203Y; S72A/S65G/V68L/T203Y; S65G/S72A/T203Y; or S65G/S72A/T203W. In another embodiment, the nucleotide sequence encoding the protein differs from the nucleotide sequence of native green fluorescent protein by the substitution of at least one codon encoding an amino acid substitution at L42, V61, T62, V68, Q69, Q94, N121, Y145, H148, V150, F165, I167, Q183, N185, L220, E222 (not E222G), or V224. In another embodiment, the amino acid substitution is: L42X, wherein X is selected from C, F, H, W and Y, V61 X, wherein X is selected from F, Y, H and C, T62X, wherein X is selected from A, V, F, S, D, N, Q, Y, H and C, V68X, wherein X is selected from F, Y and H, Q69X, wherein X is selected from K, R, E and G, Q94X, wherein X is selected from D, E, H, K and N, N121X, wherein X is selected from F, H, W and Y, Y145X, wherein X is selected from W, C, F, L, E, H, K and Q, H148X, wherein X is selected from F, Y, N, K, Q and R, V150X, wherein X is selected from F, Y and H, F165X, wherein X is selected from H, Q, W and Y, I167x, wherein X is selected from F, Y and H, Q183X, wherein X is selected from H, Y, E and K, N185X, wherein X is selected from D, E, H, K and Q, L220X, wherein X is selected from H, N, Q and T, E222X, wherein X is selected from N and Q, or V224X, wherein X is selected from H, N, Q, T, F, W and Y. These examples are merely illustrative of the wide selection of fluorescent polypeptides and their corresponding polynucleotide sequences that may be employed in the preparation of the genetically-modified cells or animals of the invention.

Another example of a fluorescent protein is red fluorescent protein from coral (Matz et. al., 1999, *Nature Biotechnology* 17:969). Fluorescent peptides or fluorescent protein fragments of these and other fluorescent proteins are also embraced herein. In another example of a detectable polypeptide, polypeptide labels capable of being detected include those containing four cysteines at the i, i+1, i+4, and i+5 positions (i.e., WEAAAREACCRECCARA (SEQ ID NO: 1). These peptides will bind specifically to the fluorescein derivative 4',5'-bis(1,3,2-dithioarsolan-2-yl)fluorescein (FLASH), which is non-fluorescent until bound. The use of such peptides has the advantage of providing fusion proteins of much smaller size than GFP, and fluorescence is easily detected by addition of FLASH (Griffin et. al., 1998, *Science* 281:269). Thus, the use of polypeptides that are capable of specifically binding a detectable label are embraced herein as another embodiment of the present invention.

Examples of polypeptides capable of being detected by enzymatic activity include various enzymes and catalytic polypeptide fragments thereof. Particularly preferred enzymatic labels include those which are able to produce a detectable color or fluorophore in a single step requiring a minimum or reagents, such as alkaline phosphatase, which can cleave a chromogenic substrate, such as p-nitrophenyl phosphate, or a fluorigenic substrate, such as ECF substrate (Amersham/Pharmacia); and a fluorigenic horseradish peroxidase substrate, FluoroBlot (Pierce Chemical Co.). Another example is a fluorescent beta-galactosidase substrate that can be used in live cells and is 100-fold more sensitive than GFP (Zlokarnik et. al., 1988, *Science* 279:85). The skilled artisan by the teachings herein will be amply aware of polynucleotides that may be fused to the immunoglobulin constant region(s) and upon expression produce an enzymatically-active fusion polypeptide comprising the immunoglobulin heavy and/or light chain.

Such labels may also result in the precipitation of a substrate, for histochemical localization of the antibody, or the label may interact with another detectable component, ands thus be, for example, an intein, a biotin-binding subunit of streptavidin or avidin, a His tag, or a chitin-binding domain.

Guidance for the selection of the immunoglobulin genes and locations therein in which to fuse the detectable polypeptide(s) of the invention may be performed as follows. As is well known, the antibody molecule is composed of two heavy chains and two light chains. Each chain has a two identical variable regions which bind antigen, and a constant region. The N-terminus of both chains is part of the variable region and the C-terminus is part of the constant region.

The genomic organization of heavy chain contains a number of repeats of V, D, and J regions upstream of several constant regions. The different constant regions define the eventual antibody class (e.g., IgG1, IgG2a, IgA, etc). During B-cell maturation, a single V, D, and J are joined to form a single exon. Additionally, late in B-cell development, a single constant region is chosen in a process called "class switching". Each constant region contains a number of exons. After transcription, the VDJ and constant regions are spliced into the mature mRNA.

To generate the fusion protein of the invention, a polynucleotide encoding the detectable polypeptide is inserted into the constant region, or preferably, is appended to portion of the gene resulting in the expression of the fused polypeptide label on the C-terminus of the constant region of the light and/or heavy chains, optionally with a flexible linker peptide.

There are two classes of light chains, kappa and lambda. Kappa comprises 95% of antibodies, lambda 5%. Furthermore, there are two forms of each class of the heavy chain—a secreted and a membrane bound form. The membrane bound form is responsible for signaling to the B-cell when it is crosslinked by an antigen and is required for B-cell maturation and antibody production. The two forms result from alternative splicing. Preferably, only the secreted form is modified as described herein. The membrane bound form would be completely wild type, to maintain fidelity of generation of the antibody response.

Thus, an immune cell with the genetic modifications described herein may secrete immunoglobulin that may have possess a detectable polypeptide label fused in the heavy chain constant region, or a detectable polypeptide label fused in the light chain constant region, or the immunoglobulin may have both a heavy and light chain fusion component. Moreover, each detectable label may be a single detectable label or a plurality of labels, in tandem or not, optionally separated from the immunoglobulin portion of the polypeptide by one or more linker sequences. The label on the heavy chain may be the same or different from that on the light chain, for immunoglobulins that have both heavy and light chains as fusion products. Although the placement of the detectable label is preferably on or near the C-terminus, the fused label(s) may be at any position(s) with does not detract from the ability of the immunoglobulin to interact with and bind to its target antigen. The invention herein embraces any and all variations in the position, placement, linkers, and number of fused peptides or polypeptides, with the object of the invention to provide at least one detectable label on an immunglobulin molecule generated by exposure of an animal or immune cell with the aforementioned genetic modification to any immunogen capable of eliciting secretion of an antibody directed thereto.

As described above, a mammalian organism, such as a mouse, rat, rabbit, goat, cow, horse, may be provided with the genetic modification as described herein. Example 4 below demonstrates the invention using mice, in which endogenous production of fluorescent antibodies is shown. Exposure of the animal to a preselected immunogen will elicit an antibody response, the secreted antibodies having the detectable label(s) present in every antibody molecule. For production of polyclonal antibodies, antiserum from the immunized animals may be collected, the antibodies purified if desired, for subsequent use in such areas as histochemistry, diagnostics, etc.

If detectably-labeled primary monoclonal antibodies are desired, routine methods may be followed using an animal, such as a mouse, with the genetic makeup hereindescribed. B-cells secreting the detectably-labeled primary antibodies may be fused for immortalization, and screening and selection for stable antibody-secreting hybridomas obtained by routine methods.

Of course, detectably-labeled primary anti-idiotype antibodies may be prepared by the foregoing methods, using antibodies as immunogen.

As mentioned above, the polyclonal and monoclonal antibodies generated by the methods described herein have several advantages, including 1) because the primary antibody is endogenously fluorescent, no secondary antibody or chemical labeling is required, 2) autofluorescent proteins are currently available in several different colors, including blue, cyan, green, yellow, and red, allowing for simultaneous labeling of several antigens, and simultaneous detection by instrumentation capable of discriminating several fluorophores simultaneously. In addition, the availability of two different means for detection, such as but not limited to a visibly-detectable and enzymatically-detectable marker, provides detectability under a variety of conditions, applicable to various research and diagnostic applications, among others.

Introduction of the genetic modification(s) described herein into an embryonic stem cell or other cell type may be achieved by a variety of procedures known in the art. Preferably, the genetic modification is introduced by a "knock-in" procedure in which the wild-type immunoglobulin gene(s) are replaced by the detectable-label-modified genes. Such procedures may include the use of a bacterial artificial chromosome, as exemplified in Example 2 below, although this example is merely illustrative and non limiting as to procedures for achieving the genetically-modified mammal or mammalian cells of the invention.

Antigens to which detectable antibodies may be raised in genetically-modified animals or immune cells as described herein are not limited to any particular types or classes of immunogen, and includes those for which a detectable antibody is desirable. Such antigens comprise a vast list. By way of non-limiting example, this includes diagnostic and research reagents for identifying the presence of and/or quantitating various medically-important biomolecules in bodily fluids, biopsy and necropsy samples, for example, all diagnostic tests which employ immunoassay protocols, including ELISA, radioimmunoassay, EMIT, immunofluorescence, fluorescence polarization, and other methods for detecting the interaction between and biomolecule of interest and an antibody thereto. Medical diagnostics include, by way of non-limiting example, assays for autoimmune disorders, cardiovascular disorders, diabetes, endocrine disorders, fungal, bacterial, viral, parasitic, and other infectious agents, hematologic diseases, immunologic diseases, hepatic diseases, oncologic diseases, thyroid diseases, and toxicology and drugs of use and abuse. Moreover, as mentioned above, the ability to discriminate between differently labeled primary antibodies without the need for, and concomitant disintegration of signal, by multiple secondary antibodies, will permit multiple analytes to be measured simultaneously, decreasing the costs and increasing the amount of information available for rendering diagnostic and therapeutic decisions. In the research area, innumerable new and known biomolecules to which antibodies are routinely raised for identifying the location, movement, transport, role, etc., of such new or rediscovered biomolecules in biological processes will be simplifiable, as well as permit the simultaneous and facile monitoring of multiple biomolecules using differently-labeled antibodies to several biomolecules participating in a process. The discussion herein on particular antigens is not intended to be at all limiting but is merely illustrative of some examples of the utility of the invention.

In another example of the invention, a genetically-modified mammal may be prepared which responds to immunization with an antigen by the production of chimeric immunoglobulin molecules capable of reading out a signal or altering the signal produced only on binding with the target antigen. This signal may be, for example, an increase, decrease or change in fluorescence. Such chimeric antibodies may be used in a very simple homogeneous immunoassay in which, on combining with a sample, indicates the presence or extent of the level of the antigen in the sample. Pairs of proteins or peptides capable of undergoing such modulation in fluorescence include FRET pairs, such as described, for example, in U.S. Pat. No. 5,998,204, incorporated herein by reference in its entirety.

Such chimeric antibodies are prepared by following the methods described herein. In the example wherein the fluorescence is detected, the genes encoding the chains of the secreted immunoglobulin are modified at the polynucleotide level to provide that both a fluorescent peptide or polypeptide, and a fluorescence-quenching or -modulating peptide or polypeptide, are fused into either the heavy immunoglobulin chain or the light immunoglobulin chain in the appropriate position in the genome of the mouse. The positions of integration into the respective immunoglobulin components are such that the proximity of the fluorescent polypeptide and the fluorescence-quenching or -modulating polypeptide in the secreted, whole immunoglobulin molecule, change on binding of the immunoglobulin to its target antigen. This change in proximity alters the interaction between the fluorophore and the quencher or modulator resulting in a modulation in the detectable fluorescence on exposure of the immunoglobulin to its excitation wavelength. Such positions are selected to not alter the ability of the complete immunoglobulin molecule to assemble, be secreted, or bind the antigen. These selections are within the realm of the skilled artisan. Known fluorescent peptides or polypeptides as well as peptides and polypeptides capable of quenching or modulating the fluorescence, such as FRET pairs, are known and can be selected to provide the chimeric immunoglobulin, and mammals capable of producing the immunoglobulin after immunization.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Secretion of Detectably-Labeled Antibodies

A rat IgG2A antibody hybridoma which produces a monoclonal antibody reactive against beta-galactosidase was used to determining whether GFP fusion proteins would be correctly assembled, secreted, and recognize antigen. The cDNA of the secreted form of the heavy and light chains against beta-galactosidase were cloned. The polynucleotide sequence encoding GFP was placed in front of the stop codon of both the heavy chain of IgG2A and light kappa chains. The plasmid combinations of 1) non-GFP tagged, 2) IgG2A heavy chain tagged, 3) light chain tagged, and 4) both heavy chain and light chain tagged, were transfected into 293T kidney cells and tested for ability to bind antigen.

The 293T cells do not express any endogenous antibodies. They were transfected with two expression vectors of combinations of IgG2A and kappa chains against beta-galactosidase: 1) IgG2A and kappa; 2) IgG2A and kappa-GFP; 3) IgG2A-GFP and kappa; and 4) IgG2A-GFP and kappa-GFP. The transfected cells will express and assemble and secrete the complete antibody. Forty-eight hours after transfection, the medium was harvested. This contained unpurified antibodies which was used for the experiments below Confirmation of the secretion of the detectably-labeled antibody was obtained in several experiments. In one experiment, cells were fed radiolabeled $^{35}$S methionine after transfection and newly synthesized proteins were labeled. The secreted proteins were collected. Two fractions were evaluated, one that bound to Protein G and one that bound to beta-galactosidase immobilized on beads. Protein G is a toxin which binds antibodies. As shown in FIG. 1, both GFP-tagged and untagged antibodies bound to Protein G and to beta-galactosidase. The affinity and specificity towards beta-galactosidase appears greater. Thus, the antibody recognizes antigen and is correctly folded. When only light chain or heavy chain but not both are transfected, the chains did not bind to either protein G or beta-galactosidase. When examined under the microscope, the beads where bright green, showing that the GFP is correctly folded and fluorescent.

EXAMPLE 2

Preparation of Genetically-Modified (Knock-In) Animals Comprising Detectably-Labeled Immunoglobulin Genes Knock-in or gene replacement involves replacing an endogenous piece of DNA in the chromosome with a constructed piece of DNA. Thus, the constructed DNA must correctly integrate into the same genetic location as the gene to be replaced. This is distinctly different from transgenic technology where a constructed DNA is randomly introduced into a cell.

I. Construction of a segment of bacterial plasmid DNA that contains the change of interest and extensive homology to the target. Generation of the IgG1-GFP fusion knock-in construct is described below. The VDJ variable regions of the IgG1 constant chain are far upstream (5') of this area. Immediately upstream of this area are the IgM and IgD constant regions. Downstream to this area are the constant regions for IgG2a, IgG2b, IgG3, IgE, and IgA. The exons CH1, CH2 and G1 are spliced together to make the constant region of the secreted form. To make the membrane bound form, CH1, CH2, G1 (except the last 2 amino acids), TD1, and TD2 are spliced together. In the targeting vector, GFP is fused in-frame at the end of the G1 exon with a five-amino-acid linker of Gly-Gly-Ser-Gly-Gly (SEQ ID NO: 2) in-between. The membrane bound form splices out the last two amino acids of G1 and thus the entire GFP. Therefore, GFP will be fused only to the secreted form.

A bacterial artificial chromosome (BAC) containing the entire IgG region is obtained. The targeting vector contains the 5' homologous region directly PCRed from the BAC. The G1-GFP fusion is generated by primer overlap extension PCR (Horton et al., 1990; Horton, 1995). A neomycin resistance gene is introduced as a selection marker. This neomycin gene is flanked on each side by a loxP site. Thus, after selection, the gene is deleted by Cre-mediated recombination. This eliminates problems due the presence of the neomycin gene and its associated promoter (Zou et al., 1993). A 3' homologous region is also PCRed from the BAC. Finally, a toxic gene, diphtheria toxin (DTA) is introduced just outside the area of homology. Homologous recombination between the targeting vector and the targeting region cuts out the toxin gene. Non-homologous random integration events often retain DTA and the cells will be killed (Yagi et al., 1990; Yagi et al., 1993; McCarrick, III et al., 1993).

After preparation, embryonic stem cells are transfected with the targeting vector and selection with neomycin analog G418 is performed. Clones are screened for correct integration by Southern analysis and PCR. Subsequently, correctly targeted ES cell are injected into blastocysts and implanted into mothers. The blastocysts develop into chimeric mice, where some cells are developed from the injected ES cells. The chimeras are used to parent heterozygote mice. Two heterozygous mice are then parented to produce homozygous mice.

The mouse IgG1 heavy chain and kappa light chains have been previously targeted for gene replacement. In those cases, the constant chain was replaced with human constant chains and the resulting mice generated humanized antibodies (Zou et al., 1993; Zou et al., 1994).

Production of Monoclonal Antibodies. Mice as prepared above are inoculated with the antigen of interest. After several weeks, the antibody production against the antigen is screened, as traditionally done with an ELISA, where the antigen is immobilized, the mouse serum is added, and an enzyme-linked secondary antibody against the primary is added. The presence of enzymatic activity indicates that the mouse has produced specific antibodies. Since here, the antibodies are already fluorescent, an ELISA is unnecessary and measurement of bound fluorescence is sufficient. Fusion of splenocytes from a positive mouse with myeloma cells is used to produce immortalized antibody-producing cells, following standard protocols. Further screening of colonies can be performed using simple fluorescence measurements.

Antibody may be produced in quantity by growth of cell-hybrids, following standard protocols.

EXAMPLE 3

Homogeneous Immunoassays Using Detectably-Labeled Antibodies from a Genetically-Modified Mouse In a further example of the methods described in Example 2, above, a genetically-modified mouse may be prepared which responds to immunization with an antigen by the production of chimeric immunoglobulin molecules capable of reading out a signal only on binding with the target antigen. Such chimeric antibodies may be used in a very simple homogeneous immunoassay in which, on combining with a sample, indicates the presence or extent of the level of the antigen in the sample.

Such chimeric antibodies are prepared by following the methods herein. Both a fluorescent peptide or polypeptide, and a fluorescence-quenching peptide or polypeptide, are fused into either the heavy immunoglobulin chain or the light immunoglobulin chain in the appropriate position in the genome of the mouse. Such pairs may include FRET pairs or proteins, such as described, for example, in U.S. Pat. No. 5,998,204, incorporated herein by reference in its entirety. The positions of integration into the respective immunoglobulin components are such that the proximity of the fluorescent polypeptide and the fluorescence-quenching polypeptide change on binding of the immunoglobulin to its target antigen. Such positions also do not alter the ability of the complete immunoglobulin molecule to assemble, be secreted, or bind the antigen. Both the fluorescent and the fluorescence-quenching protein or peptides may be fused into the same immunoglobulin component, at positions wherein antigen binding induces a conformational change and thus a proximity change among the pair and attendant modulation of fluorescence.

Examples of fluorescent peptides and proteins are described above. In this example, the mouse was genetically modified such that IgG2 heavy chains included the). Suitable pairs, for example include a blue-shifted GFP mutant P4-3 (Y66H/Y145F) as the donor, and an improved green mutant S65T can respectively serve as a donor and an acceptor for fluorescence resonance energy transfer (FRET; Tsien et al., 1993, Trends Cell Biol. 3:242–245). A genetically-modified mouse expressing antibodies with these modifications was immunized with human chorionic gonadotropin (hCG). The fluorescence of antibodies produced by this mouse was increased upon binding to hCG. This reagent was used in a simplified assay in an automated fluorescence-based instrument for determining pregnancy among a large battery of other diagnostic tests on blood and urine samples.

EXAMPLE 4

Kappa-GFP Knock-In Mice Produce Fluorescent Endogenous Antibodies

Figure 2:
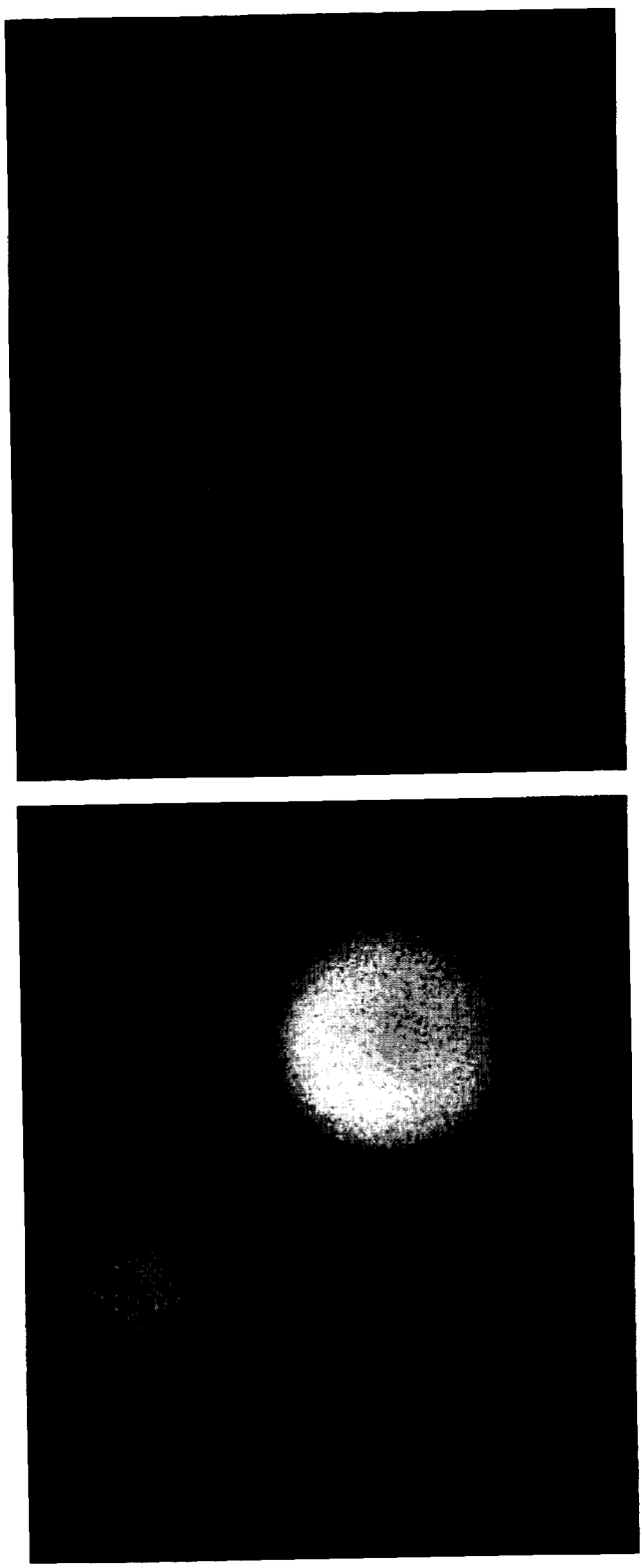
FIGS. 2 A–B show the fluorescence of antibodies in serum from kappa-GFP knock-in mice bound to Protein A/G beads, as compared to those from wild-type mice.

Kappa-GFP knock-in mice were prepared in accordance with the methods described in Example 2, above. At 8 weeks of age, animals were bled and serum was incubated with Protein A/G beads, to which antibodies in the serum bind. As shown in FIG. 2, under fluorescence illumination the beads showed the characteristic fluorescence of GFP (FIG. 2A), whereas serum from wild-type mice incubated with Protein A/G beads did not (FIG. 2B). Thus, the mice produced fluorescently-labeled, endogenous immunoglobulin molecules, comprising kappa-GFP, fluorescent light chains.

EXAMPLE 5

Confirmation of Genotype Using PCR for Kappa and GFP

Figure 3:
FIG. 3 A–B demonstrate using PCR amplification that mice of the invention may be homozygous or heterozygous for the kappa-GFP gene, using kappa light chain primers (FIG. 3A). Use of GFP primers (FIG. 3B) confirm the presence or absence of the GFP insert.
Figure 3:
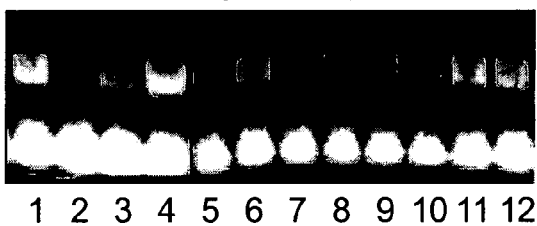

FIG. 3 shows the results of PCR amplification using primers from up- and down-stream of the section of the kappa light chain where the GFP was targeted (FIG. 3A), or using GFP primers (FIG. 3B), from DNA extracts from a number of mice prepared in accordance with the present invention. The segment amplified from wild type kappa light chains is the smallest and runs the fastest on the gel (as indicated). The segment amplified with the GFP insert is larger and migrates slower.

In FIG. 3A, using the kappa primers, lane 2 has only the faster moving product and is therefore from a mouse that is homozygous for wild-type kappa light chain. Lanes 3, 5, and 7–12 have both products, which indicates that the mice are heterozygous. Lanes 1, 4, and 6 only have the slower moving product indicating that they are homozygous for the kappa with the inserted GFP.

FIG. 3B shows using primers from the GFP coding region that lane 2 was negative for GFP, consistent with the observation that this mouse did not produce a PCR product from kappa-GFP. Lanes 1 and 2–12 were positive for GFP, consistent with the results from the top panel.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

Horton, R. M. (1995). PCR-mediated recombination and mutagenesis. SOEing together tailor-made genes. Mol. Biotechnol. 3, 93–99.

Horton, R. M., Cai, Z. L., Ho, S. N., and Pease, L. R. (1990). Gene splicing by overlap extension: tailor-made genes using the polymerase chain reaction. Biotechniques 8, 528–535.

McCarrick, J. W., III, Parnes, J. R., Seong, R. H., Solter, D., and Knowles, B. B. (1993). Positive-negative selection gene targeting with the diphtheria toxin A-chain gene in mouse embryonic stem cells. Transgenic Res. 2, 183–190.

Yagi, T., Ikawa, Y., Yoshida, K., Shigetani, Y., Takeda, N., Mabuchi, I., Yamamoto, T., and Aizawa, S. (1990). Homologous recombination at c-fyn locus of mouse embryonic stem cells with use of diphtheria toxin A-fragment gene in negative selection. Proc. Natl. Acad. Sci. U.S.A 87, 9918–9922.

Yagi, T., Nada, S., Watanabe, N., Tamemoto, H., Kohmura, N., Ikawa, Y., and Aizawa, S. (1993). A novel negative selection for homologous recombinants using diphtheria toxin A fragment gene. Anal. Biochem. 214, 77–86.

Zou, Y. R., Gu, H., and Rajewsky, K. (1993). Generation of a mouse strain that produces immunoglobulin kappa chains with human constant regions [see comments]. Science 262, 1271–1274.

Zou, Y. R., Muller, W., Gu, H., and Rajewsky, K. (1994). Cre-loxP-mediated gene replacement: a mouse strain producing humanized antibodies. Curr. Biol. 4, 1099–1103.

What is claimed is:

1. A genetically-modified mouse whose genome comprises a single vector comprising a fusion polynucleotide, said fusion polynucleotide comprising a nucleic acid encoding an immunoglobulin component selected from the group consisting of the kappa immunoglobulin light chain, the lambda immunoglobulin light chain, an immunoglobulin heavy chain, and any combination thereof, and a nucleic acid encoding at least two detectable proteins, wherein said mouse is capable of expressing at least two detectable proteins fused with said immunoglobulin component wherein an antibody secreted by an immune cell of said genetically-modified mouse comprises said at least two detectable proteins.

2. The genetically-modified mouse of claim 1 wherein said at least two detectable proteins encoded by the fusion polynucleotide are present at the C-terminus of the gene product of said fusion polynucleotide.

3. The genetically-modified mouse of claim 2 wherein said nucleic acid encoding said at least two detectable proteins present at the C-terminus of the gene product of said fusion polynucleotide is located in exon G1.

4. The genetically-modified mouse of claim 1 wherein said at least two detectable proteins are present at the C-terminus of the gene product of said fusion polynucleotide with a flexible linker peptide located between the at least two detectable proteins and the immunoglobulin component.

5. The genetically-modified mouse of claim 1 wherein said immunoglobulin heavy chain is selected from the group consisting of IgG, IgM, IgD and IgA.

6. The genetically-modified mouse of claim 1 wherein an antibody secreted by an immune cell of said genetically-modified mouse comprises at least two detectable proteins in the heavy chain of said antibody.

7. The genetically-modified mouse of claim 1 wherein an antibody secreted by an immune cell of said genetically-modified mouse comprises at least two detectable proteins in the light chain of said antibody.

8. The genetically-modified mouse of claim 1 wherein an antibody secreted by an immune cell of said genetically-modified mouse comprises at least two detectable proteins in the heavy chain and at least two detectable proteins in the light chain of said antibody.

9. The genetically-modified mouse of claim 1 wherein one of the at least two detectable proteins is capable of quenching fluorescence.

10. The genetically-modified mouse of claim 1 wherein at least one of the at least two detectable proteins is an autofluorescent protein, a visibly-detectable protein, an enzymatically active protein, or a protein capable of interacting with another molecule to produce a detectable product.

11. The genetically-modified mouse of claim 10 wherein said at least one of the at least two detectable proteins is an autofluorescent protein.

12. The genetically-modified mouse of claim 10 wherein said autofluorescent protein is selected from the group consisting of green fluorescent protein, cyan fluorescent protein, yellow fluorescent protein, red fluorescent protein, and a fluorescent analog or fragment of any of the foregoing.

13. The genetically-modified mouse of claim 11 wherein said autofluorescent protein is green fluorescent protein.

14. The genetically-modified mouse of claim 10 wherein said at least one detectable protein is a combination of an autofluorescent protein and an enzymatically-active protein.

15. The genetically-modified mouse of claim 14 wherein said at least one detectable protein is a combination of green fluorescent protein and alkaline phosphatase.

16. A genetically-modified immune cell having a single vector comprising a fusion polynucleotide, said fusion polynucleotide comprising a nucleic acid encoding an immunoglobulin component selected from the group consisting of the kappa immunoglobulin light chain, the lambda immunoglobulin light chain, an immunoglobulin heavy chain, and any combination thereof, nucleic acid encoding at least two detectable proteins, and a nucleic acid encoding a flexible linker peptide located between the nucleic acid encoding the immunoglobulin component and the nucleic acid encoding the at least two detectable proteins, and wherein said immune cell is capable of expressing at least two detectable proteins fused with said immunoglobulin component, with the flexible linker peptide between the immunoglobulin component and the at least two detectable proteins, wherein antibodies secreted by said genetically-modified immune cell comprise said at least two detectable proteins.

17. The genetically-modified immune cell of claim 16 wherein said at least two detectable proteins are present at the C-terminus of the gene product of said fusion polynucleotide.

18. The genetically-modified immune cell of claim 16 wherein said nucleic acid encoding said at least two detectable proteins present at the C-terminus of the gene product of said fusion polynucleotide is located in exon G1.

19. The genetically-modified immune cell of claim 16 wherein said immunoglobulin heavy chain is selected from the group consisting of IgG, IgM, IgD and IgA.

20. The genetically-modified immune cell of claim 16 wherein an antibody secreted by said immune cell comprises at least two detectable proteins in the heavy chain of said antibody.

21. The genetically-modified immune cell of claim 16 wherein an antibody secreted by said genetically-modified immune cells comprises at least two detectable proteins in the light chain of said antibody.

22. The genetically-modified immune cell of claim 16 wherein an antibody secreted by said genetically-modified immune cells comprises at least two detectable proteins in the heavy chain and at least two detectable proteins in the light chain of said antibody.

23. The genetically-modified immune cell of claim 16 wherein one of the at least two detectable proteins is capable of quenching fluorescence.

24. The genetically-modified immune cell of claim 16 wherein at least one of the at least two detectable proteins is an autofluorescent protein or peptide, a visibly-detectable protein or peptide, an enzymatically active protein or peptide, or a protein or peptide capable of interacting with another molecule to produce a detectable product.

25. The genetically-modified immune cell of claim 24 wherein said at least one of the at least two detectable proteins is an autofluorescent protein.

26. The genetically-modified immune cell of claim 25 wherein said autofluorescent protein is selected from the group consisting of green fluorescent protein, red fluorescent protein, and a fluorescent analog or fragment of any of the foregoing.

27. The genetically-modified immune cell of claim 26 wherein said autofluorescent protein is green fluorescent protein.

28. The genetically-modified immune cell of claim 24 wherein said at least one detectable protein is a combination of an autofluorescent protein and an enzymatically-active protein.

29. The genetically-modified immune cell of claim 28 wherein said at least one detectable protein is a combination of green fluorescent protein and alkaline phosphatase.

30. A genetically-modified mouse capable of producing a detectably-labeled antibody in response to immunization by an antigen, the genome of said non-human mouse comprising at least one fusion polynucleotide comprising a nucleic acid encoding at least two detectable proteins and a nucleic acid encoding an immunoglobulin component selected from the group consisting of the kappa immunoglobulin light chain, the lambda immunoglobulin light chain, an immunoglobulin heavy chain, and any combination thereof, wherein an antibody secreted by an immune cell of said genetically-modified non-human mouse comprises said at least two detectable proteins.

31. The genetically modified mouse of claim 10 or the genetically modified immune cell of claim 24, wherein said protein capable of interacting with another molecule to produce a detectable product is selected from the group consisting of an intein, a biotin-binding subunit of streptavidin or avidin, a His tag, or a chitin-binding domain, or any combination thereof, and wherein said protein capable of interacting with another molecule to produce a detectable product may also be used to facilitate purification of said detectable product.

* * * * *

SEQUENCE LISTING

<160> NUMBER OF SEQ ID NOS: 2

<210> SEQ ID NO 1
<211> LENGTH: 17

-continued

```
<212> TYPE: PRT
<213> ORGANISM: Artificial Sequence
<220> FEATURE:
<223> OTHER INFORMATION: synthetic

<400> SEQUENCE: 1

Trp Glu Ala Ala Ala Arg Glu Ala Cys Cys Arg Glu Cys Cys Ala Arg
 1               5                  10                  15

Ala

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Gly Gly Ser Gly Gly
 1               5
```